United States Patent [19]

Haga et al.

[11] Patent Number: 4,987,135

[45] Date of Patent: Jan. 22, 1991

[54] SUBSTITUTED BENZENE DERIVATIVES, PROCESSES FOR THEIR PRODUCTION AND ANTITUMOR COMPOSITIONS CONTAINING THEM

[75] Inventors: Takahiro Haga; Nobutoshi Yamada; Hideo Sugi; Toru Koyanagi; Hiroshi Okada, all of Kusatsu, Japan

[73] Assignee: Ishihara Sangyo Kaisha Ltd., Osaka, Japan

[21] Appl. No.: 324,559

[22] Filed: Mar. 16, 1989

[30] Foreign Application Priority Data

Mar. 31, 1988 [JP] Japan .................. 63-79658
Feb. 14, 1989 [JP] Japan .................. 63-34487

[51] Int. Cl.$^5$ .................. A61K 31/505; C07D 239/34; C07D 401/12; C07D 403/12
[52] U.S. Cl. .................. 514/274; 514/235.8; 514/234.8; 514/249; 514/86; 514/272; 544/243; 544/323; 544/329; 544/332; 544/327; 544/296; 544/315; 544/316; 544/123; 544/119; 544/295
[58] Field of Search .................. 514/272, 86, 249, 274, 514/235.8, 234.8; 544/243, 323, 329, 332, 327, 295, 296, 315, 316, 123, 119

[56] References Cited

U.S. PATENT DOCUMENTS

| 4,200,653 | 4/1980 | Huff et al. ............... 424/322 |
| 4,623,658 | 11/1986 | Anderson et al. ............... 514/482 |
| 4,666,942 | 5/1987 | Anderson et al. ............... 514/594 |
| 4,672,139 | 6/1987 | Anderson et al. ............... 560/16 |
| 4,698,365 | 10/1987 | Anderson et al. ............... 514/594 |

FOREIGN PATENT DOCUMENTS

| 892042 | 8/1982 | Belgium . |
| 109211 | 10/1983 | European Pat. Off. . |
| 138772 | 4/1985 | European Pat. Off. . |
| 193249 | 9/1986 | European Pat. Off. . |
| 63-277664 | 11/1988 | Japan . |

Primary Examiner—John M. Ford
Attorney, Agent, or Firm—Oblon, Spivak, McClelland, Maier & Neustadt

[57] ABSTRACT

A substituted benzene derivative represented by a formula:

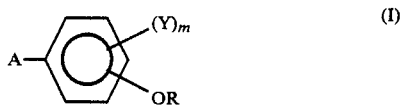

where A represents:

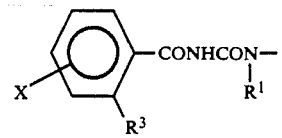

wherein X is a hydrogen atom, a halogen atom or a nitro group, $R^1$ is —$X^1Z^1$ ($X^1$ is an oxygen atom or a sulfur atom and $Z^1$ is a substituted or unsubstituted alkyl group, a substituted or unsubstituted alkenyl group, a substituted or unsubstituted alkynyl group, a substituted or unsubstituted aryl group or a substituted or unsubstituted heteroaryl group), —$COZ^1$ group ($Z^1$ is as defined above),

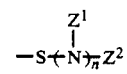

group ($Z^1$ is as defined above, $Z^2$ is —$CO_2Z^3$ wherein $Z^3$ is the same as $Z^1$, or —$SO_2Z^3$ wherein $Z^3$ is as defined above and n is 0 or 1),

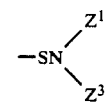

($Z^1$ and $Z^3$ are as defined above) or

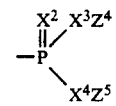

($X^2$, $X^3$ and $X^4$ are, respectively, an oxygen atom or a sulfur atom and $Z^4$ and $Z^5$ are the same as $Z^1$), and $R^3$ is a nitro group or

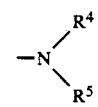

($R^4$ and $R^5$ are, respectively, an alkyl group, or they may form a heterocyclic group together with the adjacent nitrogen atom), or

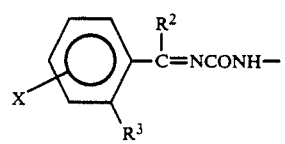

wherein X and $R^3$ are as defined above and $R^2$ is —$X^1Z^1$ ($X^1$ and $Z^1$ are as defined above); Y is a halogen atom, a substituted or unsubstituted alkyl group, a sub- (Abstract continued on next page.)

stituted or unsubstituted alkoxy group, a substituted or unsubstituted alkylthio group, a nitro group or
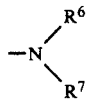
($R^6$ and $R^7$ are, respectively, a substituted or unsubstituted alkyl group); R is
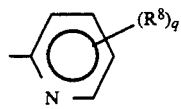
($R^8$ is the same as Y and q is an integer of 1 to 4),
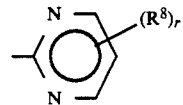
($R^8$ is as defined above, and r is an integer of 1 to 3) or
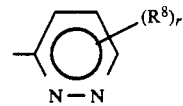
($R^8$ and r are defined above); and m is an integer, of 1 to 4, or its salt.
12 Claims, No Drawings

SUBSTITUTED BENZENE DERIVATIVES, PROCESSES FOR THEIR PRODUCTION AND ANTITUMOR COMPOSITIONS CONTAINING THEM

The present invention relates to novel substituted benzene derivatives including benzoylurea type compounds and benzimidate type compounds, processes for their production, intermediates thereof, a composition for treating leukemia, melanoma, sarcoma or carcinoma comprising the substituted benzene derivatives and a method of treating leukemia or the like as mentioned above.

Various benzoylurea type compounds and benzimidate type compounds have been disclosed in many publications. For example, certain benzoylurea type compounds have been disclosed in U.S. Pat. Nos. 4,623,658, 4,672,139, 4,666,942, 4,698,365 and Japanese Unexamined Patent Publication No. 277664/88. Certain benzimidate compounds are disclosed in U.S. Pat. No. 4,200,653, European Patent Publications No. 109,211 and No. 138,772 and Belgian Patent No 892,042. However, the compounds disclosed in these publications are different in their chemical structures from the compounds of the present invention in that the phenyl group constituting the benzoylurea or the benzimidate, has a substituent different from that of the substituted benzene derivatives of the present invention. Further, the above publications do not teach the use of the compounds of the present invention.

Further, European Patent Publication No. 193,249 discloses a certain benzoylurea type compound and the use of the compound as an antitumour agent. However, the compound disclosed in the publication is different in the chemical structure from the compound of the present invention in that the substituent on the nitrogen atom bonded to the phenyl ring is different from that of the substituted benzene derivative of the present invention.

The present inventors have conducted extensive research on the benzoylurea type compounds and the benzimidate type compounds and have found that a novel substituted benzene derivative having a nitro or substituted amino group on the phenyl group constituting the benzoylurea or the benzimidate and a specific substituent on the urea moiety or the imino moiety, exhibits excellent antitumour activities, and the poor solubility in an organic solvent observed with known compounds, is improved The present invention provides a substituted benzene derivative represented by a formula:

 (I)

where A represents:

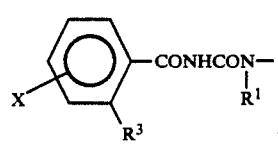

wherein X is a hydrogen atom, a halogen atom or a nitro group, $R^1$ is $-X^1Z^1$ ($X^1$ is an oxygen atom or a sulfur atom and $Z^1$ is a substituted or unsubstituted alkyl group, a substituted or unsubstituted alkenyl group, a substituted or unsubstituted alkynyl group, a substituted or unsubstituted aryl group or a substituted or unsubstituted heteroaryl group), $-COZ^1$ group ($Z^1$ is as defined above),

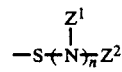

group ($Z^1$ is as defined above, $Z^2$ is $-CO_2Z^3$ wherein $Z^3$ is the same as $Z^1$, or $-SO_2Z^3$ wherein $Z^3$ is as defined above and n is 0 or 1), —SN

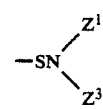

($Z^1$ and $Z^3$ are as defined above) or

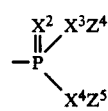

($X^2$, $X^3$ and $X^4$ are, respectively, an oxygen atom or a sulfur atom and $Z^4$ and $Z^5$ are the same as $Z^1$), and $R^3$ is a nitro group or

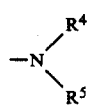

($R^4$ and $R^5$ are, respectively, an alkyl group, or they may form a heterocyclic group together with the adjacent nitrogen atom), or

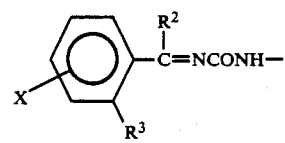

wherein X and $R^3$ are as defined above and $R^2$ is $-X^1Z^1$ ($X^1$ and $Z^1$ are as defined above); Y is a halogen atom, a substituted or unsubstituted alkyl group, a substituted or unsubstituted alkoxy group, a substituted or unsubstituted alkylthio group, a nitro group or —N

($R^6$ and $R^7$ are, respectively, a substituted or unsubstituted alkyl group); R is

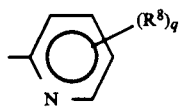

($R^8$ is the same as Y and q is an integer of 1 to 4),

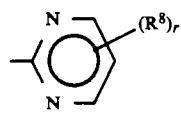

($R^8$ is as defined above, and r is an integer of 1 to 3) or

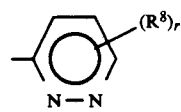

($R^8$ and r are as defined above); and m is an integer of 1 to 4, or its salt.

The present invention also provides processes for its production, intermediates thereof, a composition for treating leukemia, melanoma, sarcoma or carcinoma in mammals comprising the substituted benzene derivative, and a method of treating leukemia or the like as mentioned above.

Now, the present invention will be described in detail with reference to the preferred embodiments In the formula I, the alkyl moiety constituting the substituted or unsubstituted alkyl group, the substituted or unsubstituted alkoxy group and the substituted or unsubstituted alkylthio group in the definition of $Z^1$, $Z^3$ to $Z^5$, $R^8$ and Y, preferably includes alkyl groups having from 1 to 11 carbon atoms, such as a methyl group, an ethyl group, a propyl group, a butyl group, a pentyl group, a hexyl group, a heptyl group, an octyl group, a nonyl group, a decyl group and an undecyl group. They may be straight chain or branched aliphatic structural isomers. The substituted or unsubstituted alkyl group in the definitions of $R^4$ to $R^7$, preferably includes alkyl groups having from 1 to 6 carbon atoms such as a methyl group, an ethyl group, a propyl group, a butyl group, a pentyl group or a hexyl group. They also include structural isomers as mentioned above.

The substituted or unsubstituted alkenyl group in the definitionS of $Z^1$ and $Z^3$ to $Z^5$, preferably includes alkenyl groups having from 2 to 6 carbon atoms such as an ethenyl group, a propenyl group, a butenyl group, a pentenyl group and a hexenyl group. Further, the substituted or unsubstituted alkynyl group preferably includes alkynyl groups having 2 to 6 carbon atoms such as an ethynyl group, a propargyl group, a butynyl group, a pentynyl group and a hexynyl group. They include structural isomers as mentioned above.

The aryl group in the definitions of $Z^1$ and $Z^3$ to $Z^5$ includes a phenyl group and naphthyl group, and the heteroaryl group includes a thienyl group, a furyl group, a pyranyl group, a pyridinyl group, a pyrimidinyl group, a quinolyl group and a quinoxalinyl group.

The heterocyclic group formed by $R^4$ and $R^5$, together with the adjacent nitrogen atom in the definitions of $R^3$, includes a morpholino group, an aziridinyl group, a pyrrolidinyl group and piperidino group.

The substituent of the substituted alkyl group, the substituted alkenyl group, the substituted alkynyl group, the substituted aryl group, or the substituted heteroaryl group in the definitions of $Z^1$ and $Z^3$ to $Z^5$, includes a halogen atom, a nitro group, a cyano group, an alkyl group which may be substituted by a halogen atom, an alkenyl group which may be substituted by a halogen atom, an alkynyl group which may be substituted by a halogen atom, a cycloalkyl group which may be substituted by a halogen atom and a phenyl group which may be substituted by a halogen atom The number of these substituents may be one or more. The substituent of the substituted alkyl group, the substituted alkoxy group or the substituted alkylthio group in the definitions of Y and $R^6$ to $R^8$, includes a halogen atom, etc. The number of the substituents may be one or more.

The alkyl group as the substituent of the substituted alkyl group, the substituted alkenyl group, the substituted alkynyl group, the substituted aryl group or the substituted heteroaryl group in the definitions of $Z^1$ and $Z^3$ to $Z^5$, preferably includes alkyl groups having from 1 to 11 carbon atoms, and the alkenyl group or the alkynyl group preferably includes those having from 2 to 6 carbon atoms, respectively. Specific examples of them are the same as those of the substituted or unsubstituted alkyl group, the substituted or unsubstituted alkenyl group and the substituted or unsubstituted alkynyl group in the definition of $Z^1$. Further, the cycloalkyl group preferably includes cycloalkyl groups of from 3 to 6 carbon atoms such as a cyclopropyl group, a cyclopentyl group and a cyclohexyl group.

Further, in the formula I, $Z^3$ to $Z^5$ may be the same as defined for $Z^1$, and $R^8$ may be the same as defined for Y. However this does not mean that $Z^3$ to $Z^5$ and $Z^1$, or $R^8$ and Y are always the same at the same time. They may be the same or different to one another.

Further, when the integer of m, q or r in $(Y)_m$, $(R^8)_q$ or $(R^8)_r$ of the formula I, is 2 or more, Y and $R^8$ may be the same or different to each other.

The halogen atom in the formula I includes, for example, a fluorine atom, a chlorine atom, a bromine atom and an iodine atom.

The nitrogen atom of the —NH— moiety in the formula I is acidic, and the compound of the formula I may form a salt with an alkaline substance such as an alkali metal salt.

Among the compounds of the formula I, the following are preferred as active ingredients of antitumour compositions.

(1) A compound wherein X is a hydrogen atom.
(2) A compound wherein $R^1$ is —$SZ^1$ or —$COZ^1$.
(3) A compound wherein $R^2$ is —$OZ^1$.
(4) A compound wherein $R^3$ is a nitro group.
(5) A compound wherein Y of $(Y)_m$ is an alkyl group which may be substituted by a halogen atom and m is 1, more preferably, Y is a methyl group and m is 1.
(6) A compound wherein $(Y)_m$ (m is 1) is at the metaposition to the bonding position of A.
(7) A compound wherein R is

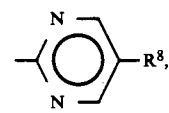

more preferably $R^8$ is a halogen atom.

(8) A compound wherein —OR is at the p-position to the bonding position of A.

Further, among the compounds of the formula I, the benzimidate compound has geometrical isomers of Z-form and E-form due to the

bond of the imino moiety. Such geometrical isomers may be obtained in the form of single substances or a mixture depending upon the method or process steps for the production.

Among the compounds of the formula I, the benzoylurea compound can be produced by the following process.

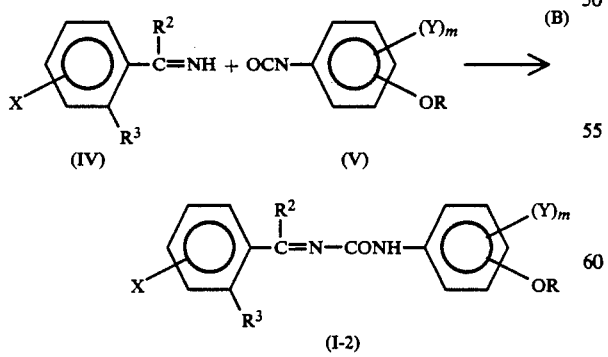

In the above formulas, X, $R^1$, $R^3$, Y, m and R are as defined above, $A^1$ is —NCO or —$NH_2$, and $A^2$ is a hydrogen atom or —COCl, provided that when $A^2$ is a hydrogen atom, $A^1$ is —NCO, or when $A^2$ is —COCl, $A^1$ is —$NH_2$. The above reaction is usually conducted at a temperature of from 0° C. to a refluxing temperature in the presence of a solvent, and the reaction time is usually from 0.1 to 70 hours. The solvent includes benzene, toluene, xylene, chlorobenzene, hexane, chloroform, methylene chloride, dichloroethane, diethyl ether, tetrahydrofuran, dioxane, ethyl acetate, dimethylformamide, dimethylsulfoxide and hexamethyl phospholic acid triamide. Further, in the case where $A^2$ is COCl and Al is —$NH_2$, the reaction is preferably conducted in the presence of a base. The base includes N-butyl lithium, triethylamine, sodium hydroxide, potassium hydroxide, sodium carbonate, potassium carbonate and sodium hydride.

Further, the benzimidate compound can be produced by the following process.

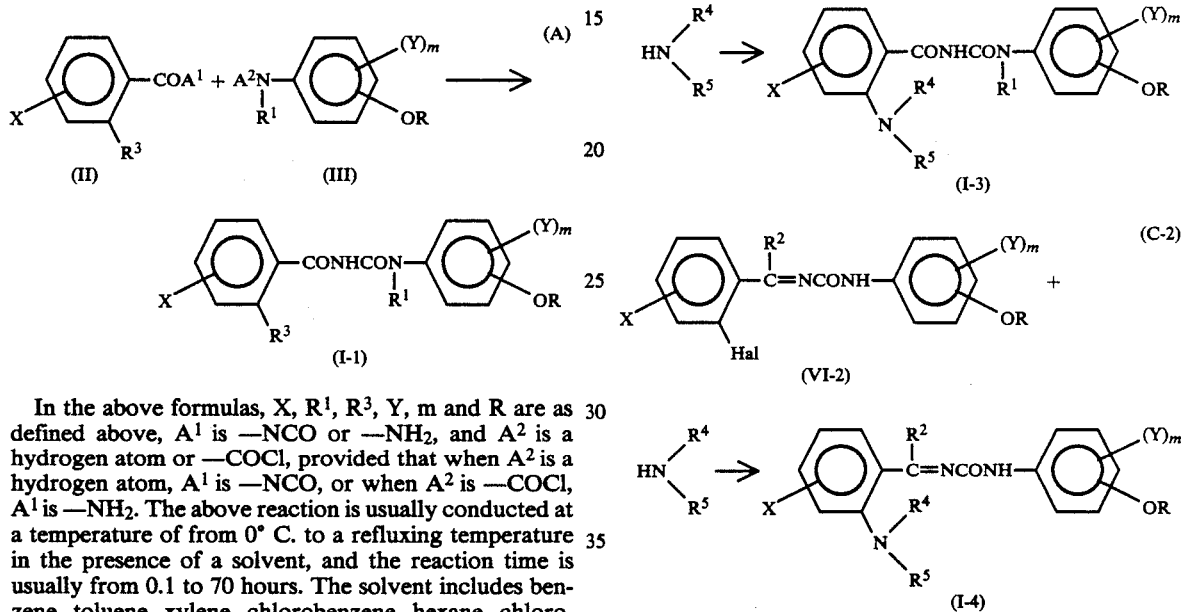

In the above formulas, X, $R^2$, $R^3$, Y, m and R are as defined above. The above reaction is usually conducted at a temperature of from 0° C. to a refluxing temperature in the presence of a solvent, and the reaction time is usually from 1 to 24 hours. As the solvent, the one useful for the process (A) may be employed.

The compound of the formula I can be prepared also by the following other processes.

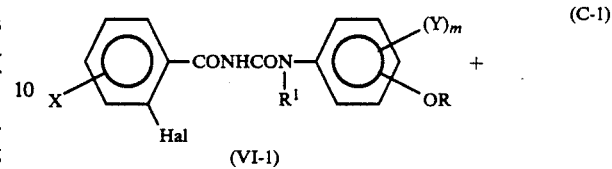

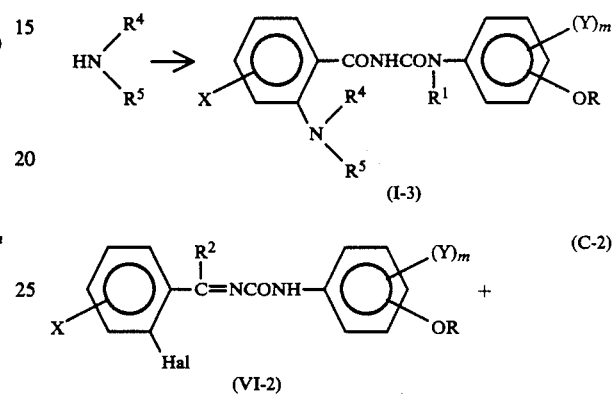

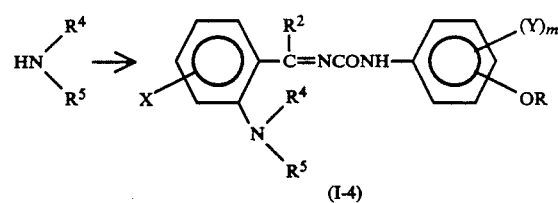

In the above formulas, X, $R^1$, $R^2$, $R^4$, $R^5$, Y m and R are as defined above, and Hal is a halogen atom.

The above reactions (C-2) are usually conducted at a temperature of from 0° C. to a refluxing temperature in the presence of a solvent, and the reaction time is usually from 1 to 24 hours. As the solvent, the one useful for the process (A) and water may be used.

The compound of the formula III used in the process (A) is a novel compound and can be prepared by e.g. the following processes.

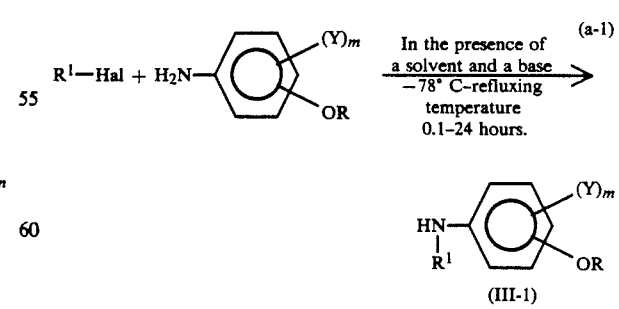

In the above formulas, $R^1$, Y, m, Hal and R are as defined above.

The solvent and the base used in the above reaction (a -1) may be the same as used in the process (A).

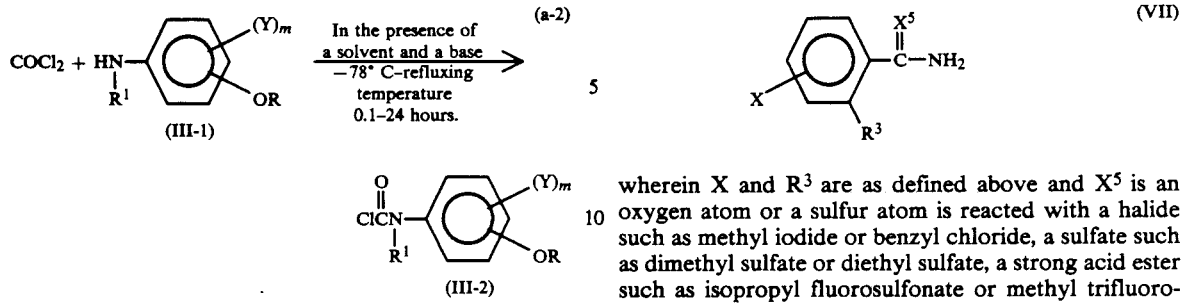

In the above formulas, $R^1$, Y, m and R are as defined above.

The solvent and the base used in the above reaction (a-2) may be the same as used in the above process (a-1).

The compound of the formula IV used in the above process (B) is also a novel compound and can be prepared by the following process.

wherein X and $R^3$ are as defined above and $X^5$ is an oxygen atom or a sulfur atom is reacted with a halide such as methyl iodide or benzyl chloride, a sulfate such as dimethyl sulfate or diethyl sulfate, a strong acid ester such as isopropyl fluorosulfonate or methyl trifluoromethanesulfonate or triethyloxonium fluoroborate $((C_2H_5)_3O+BF_4-)$ at a temperature of from $-78°$ C. to refluxing temperature for 1 to 24 hours in the presence of a solvent, to introduce $R^2$ to the compound of the formula IV. The solvent includes chloroform, methylene chloride, diethyl ether and tetrahydrofuran. Now, typical examples of the intermediate compounds of the formulas III and IV are shown in the Tables 1 and 2.

TABLE 1

| Intermediate Compound No. | $A^2$ | $R^1$ | $(Y)_m$ | $(R^8)_r$ | Physical properties Melting point (°C.) |
|---|---|---|---|---|---|
| 1 | H | —COC$_2$H$_5$ | 3-CH$_3$ | 5-Cl | 150–152 |
| 2 | " | —COC$_7$H$_{15}$(n) | " | 5-Br | 116–119 |
| 3 | " | —COC$_4$H$_9$(n) | " | " | 138–142 |
| 4 | " | —COC$_{11}$H$_{23}$(n) | " | " | 94–113 |
| 5 | " | —COC$_{10}$H$_{21}$(n) | " | " | 124–127 |
| 6 | " | —COC$_5$H$_{11}$(n) | " | " | White crystals |
| 7 | " | —COC$_5$H$_{11}$(n) | " | 5-Cl | 138–140 |
| 8 | " | —COC$_6$H$_{13}$(n) | " | 5-Br | 126–131 |
| 9 | " | —COC$_3$H$_7$(n) | " | 5-Cl | 140–143 |
| 10 | " | —COCH$_3$ | " | 5-Br | 177–180 |
| 11 | " | —COC$_3$H$_7$(n) | " | " | White crystals |
| 12 | " | —COC$_6$H$_{13}$(n) | 3-CH$_3$ | 5-Cl | 135–137 |
| 13 | " | —COC$_4$H$_9$(n) | " | " | 146–150 |
| 14 | " | —COCH$_3$ | 3-Cl | 5-Br | 212–214 |
| 15 | " | —COCH=CH$_2$ | 3-CH$_3$ | " | 172–180 |
| 16 | " | —COC≡CH | " | " | |
| 17 | " | -CO-[phenyl with O$_2$N and substituent] | 2,3-F$_2$ | " | |
| 18 | " | —COC$_4$H$_9$(n) | 3-CH$_3$ | 4,6-(CH$_3$)$_2$ | |
| 19 | " | —COCH$_2$CF$_3$ | " | 5-Br | |
| 20 | " | —COCH$_2$-[phenyl] | 3-CH$_3$ | 5-Br | |
| 21 | H | —COCH$_2$-[cyclohexyl H] | " | " | |
| 22 | " | —COC$_2$H$_5$ | " | " | |
| 23 | —COCl | " | " | " | |

TABLE 1-continued

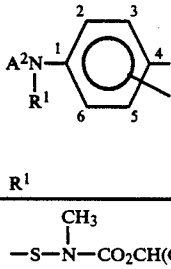

| Intermediate Compound No. | $A^2$ | $R^1$ | $(Y)_m$ | $(R^8)_r$ | Physical properties Melting point (°C.) |
|---|---|---|---|---|---|
| 24 | H | -S-N(CH$_3$)-CO$_2$CH(CH$_3$)$_2$ | " | 5-Cl | Oily substance |
| 25 | " | -S-N(C$_2$H$_5$)-SO$_2$CH$_3$ | " | " | 135-142 |
| 26 | " | -S-N(CH$_3$)-CO$_2$CH$_3$ | " | " | 90-93.5 |
| 27 | " | -S-N(C$_3$H$_7$(n))-CO$_2$CH(CH$_3$)$_2$ | " | " | Oily substance |
| 28 | " | -S-N(CH$_3$)-CO$_2$CH(CH$_3$)$_2$ | 3-Cl | 5-Br | 46-54 (Non-crystalline form) |
| 29 | " | -S-N(C$_3$H$_7$(n))-CO$_2$CH(CH$_3$)$_2$ | " | " | Oily substance |
| 30 | " | -S-N(CH$_3$)-CO$_2$-C$_6$H$_5$ | " | " | |
| 31 | " | -S-N(C$_8$H$_{17}$(n))-CO$_2$CH$_3$ | " | " | Oily substance |
| 32 | " | -S-N(CH$_3$)-CO$_2$C$_8$H$_{17}$(n) | " | " | Oily substance |
| 33 | " | -S-N(CH$_3$)-CO$_2$CH(CH$_3$)$_2$ | 3-CF$_3$ | 5-Cl | |
| 34 | H | -S-N(CH$_3$)-CO$_2$CH(CH$_3$)$_2$ | 3-NO$_2$ | 5-Br | Oily substance |
| 35 | " | -S-CO$_2$CH$_3$ | 3-CH$_3$ | 5-Cl | 90-96 |
| 36 | " | -S-C$_{10}$H$_{21}$ (n) | " | 5-Br | Oily substance |
| 37 | " | -S-(2-NO$_2$-C$_6$H$_4$) | " | 5-Cl | 74-85 (yellow non-crystalline form) |
| 38 | " | -S-C$_6$H$_5$ | " | " | Oily substance |
| 39 | " | -S-C$_6$H$_5$ | " | 5-Br | Oily substance |
| 40 | " | -S-CO$_2$CH$_3$ | 3-Cl | 5-Br | 114-116 |

TABLE 1-continued

Structure: A²N(R¹)—[phenyl(1-6, with (Y)m)]—4—O—2—[pyridinyl(1-6, with N at 3, (R⁸)r)]

| Intermediate Compound No. | A² | R¹ | (Y)m | (R⁸)r | Physical properties Melting point (°C.) |
|---|---|---|---|---|---|
| 41 | " | —S—[phenyl-NO₂] | " | " | 194–197 (yellow) |
| 42 | " | —S—C₄H₉(n) | " | " | Oily substance |
| 43 | " | —S—C₁₀H₂₁(n) | " | " | $n_D^{18.6}$ 1.5767 |
| 44 | " | —P(=S)(OC₂H₅)₂ | 3-CH₃ | " | Oily substance |
| 45 | " | —O—C₄H₉(n) | " | " | |
| 46 | " | —SCH=CH₂ | " | 4,6-(CH₃)₂ | |
| 47 | " | —SC≡CH | 2,3-F₂ | 5-Br | |
| 48 | H | —SCH₂CF₃ | 3-CH₃ | 5-Br | |
| 49 | " | —SCH₂—[cyclohexyl-H] | " | " | |
| 50 | " | —SN(CH₃)₂ | " | " | |
| 51 | " | —S—[phenyl-NC] | " | " | |
| 52 | " | —P(=O)(OC₂H₅)(OC₂H₅) | " | " | |
| 53 | " | —P(=O)(OC₂H₅)(SC₂H₅) | " | " | |
| 54 | " | —CO—[pyridinyl] | " | " | |
| 55 | —COCl | —S—C₄H₉(n) | 3-Cl | " | |

Intermediate compound No. 56:
Isopropyl [[[4-(5-nitro-2-pyridinyloxy)-3-chlorophenyl]amino]thio]-N-methylcarbamate Oily substance
Intermediate compound No. 57:
Isopropyl [[[3-(5-chloro-2-pyrimidinyloxy)-4-methylphenyl]amino]thio]-N-methylcarbamate Oily substance
Intermediate compound No 58:
Isopropyl [[[4-(6-chloro-3-chlorophenyl]amino]thio]-N-methylcarbamate Melting Point: 132°–134° C.
Intermediate compound No. 59:
N-[3-methyl-4-(4,5,6-trimethyl-2-pyridinyloxy)]propionamide

TABLE 2

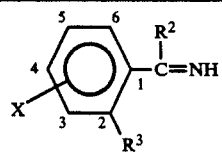

| Intermediate Compound No. | X | R³ | R² | Physical properties |
|---|---|---|---|---|
| 60 | H | NO₂ | —OCH₃ | $n_D^{20.4}$ 1.5520 |
| 61 | " | " | —OC₂H₅ | $n_D^{20.4}$ 1.5428 |
| 62 | " | " | —OC₃H₇(iso) | Melting point: 36–40° C. |
| 63 | " | " | —OC₅H₁₁(sec) | Oily substance |
| 64 | " | " | —OC₁₀H₂₁(n) | " |
| 65 | " | " | —OC₅H₁₁(n) | " |
| 66 | 4-Cl | " | —OCH₂CH=CH₂ | |
| 67 | H | " | —OCH₂C≡CH | |
| 68 | " | " | —O—⟨C₆H₄-O₂N⟩ | |
| 69 | " | " | —O—⟨pyridyl-Cl⟩ | |
| 70 | 6-F | —N(CH₃)₂ | —OC₂H₅ | |
| 71 | H | —N⟨pyrrolidinyl⟩ | " | |
| 72 | " | NO₂ | —OCH₂—⟨C₆H₁₁⟩ | |
| 73 | " | " | —OCH₂—⟨C₆H₅⟩ | |
| 74 | " | " | —OCH₂CF₃ | |
| 75 | H | NO₂ | —SCH₂—⟨C₆H₁₁⟩ | $n_D^{21.2}$ 1.6276 |
| 76 | " | " | —SCH₂CH=CH₂ | $n_D^{21.2}$ 1.5992 |
| 77 | " | " | —SCH₂C≡CH | Oily substance |
| 78 | " | " | —OCH₂—⟨C₅H₉⟩ | $n_D^{27.6}$ 1.5379 |
| 79 | " | " | —SC₂H₅ | Oily substance |

TABLE 2-continued

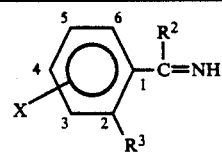

| Intermediate Compound No. | X | R³ | R² | Physical properties |
|---|---|---|---|---|
| 80 | " | " | —SC₅H₁₁(sec) | Oily substance |

Now, specific Preparation Examples of the compounds of the formulas I, III and IV will be described.

PREPARATION EXAMPLE 1

Preparation of methyl 4-[4-(5-bromo-2-pyrimidinyloxy)-3-chlorophenyl]-7-(2-nitrophenyl)-2-octyl-5,7-dioxo-3-thia2,4,6-triazaheptanate (Compound No. 31)

(1) 3.0 g of 4-(5-bromo-2-pyrimidinyloxy)-3-chloroaniline and 3.04 g of methyl N-chlorosulfenyl-N-noctylcarbamate were dissolved in 30 ml of methylene chloride, and a solution of 1.52 ml of triethylamine dissolved in 3 ml of methylene chloride was dropwise added thereto under cooling with ice. The mixture was reacted at room temperature for 3 hours. After completion of the reaction, methylene chloride was distilled off from the reaction product, and the reaction product was purified by silica gel column chromatography to obtain 4.0 g of methyl N-{[[4-(5-bromo-2-pyrimidinyloxy) -3-chlorophenyl]amino]thio}-N-n-octylcarbamate (oily substance) (Intermediate Compound No. 31).

(2) 4.0 g of the Intermediate Compound No. 31 obtained in the step (1) was dissolved in 30 ml of 1,2-dichloroethane, and 1.77 g of 2-nitrobenzoyl isocyanate was added thereto. The mixture was reacted at room temperature for 1.5 hours. After completion of the reaction, 1,2-dichloroethane was distilled off from the reaction product, and the reaction product was purified by silica gel column chromatography to obtain 2.65 g of the desired compound (melting point: 51°–54° C.) in a noncrystalline form.

PREPARATION EXAMPLE 2

Preparation of N-[4-(5-bromo-2-pyrimidinyloxy)-3-methylphenyl] O,O-diethyl N-(2-nitrobenzoylaminocarbonyl)phosphoramidothionate (Compound No. 52)

(1) To a solution of 3.0 g of 4-(5-bromo 2-pyrimidinyloxy)-3-methylaniline dissolved in 30 ml of tetrahydrofuran, a solution of 0.70 g of butyl lithium dissolved in 7.4 ml of n-hexane was dropwise added thereto at −78° C. After completion of the dropwise addition, the mixture was stirred for 15 minutes, and a solution of 2.22 g of O,O-diethylphosphorochloridothionate dissolved in 3 ml of tetrahydrofuran was dropwise added thereto. The mixture was reacted at room temperature for 2 hours. After completion of the reaction, the reaction product was poured into water and extracted with ethyl acetate. Then, the extract was dried over Glauber's salt and purified by silica gel column chromatography to obtain 1.48 g of N-[4-(5-bromo-2-pyrimidinyloxy)-3-methylphenyl] O,O-diethylphosphoramidothionate (Intermediate Compound No. 44) as oily substance.

(2) 1.48 g of the Intermediate Compound No. 44 obtained in the above step (1) and 1.32 g of 2-nitrobenzoyl isocyanate were dissolved in 20 ml of tetrahydrofuran. The mixture was reacted under reflux for 24 hours and further at room temperature for 44 hours. After completion of the reaction, the reaction product was poured into water and then extracted with ethyl acetate. The extract was dried over Glauber's salt and purified by silica gel column chromatography to obtain 1.40 g of the desired compound (melting point: 56°–60° C.).

PREPARATION EXAMPLE 3

Preparation of N-[4-(5-chloro-2-pyrimidinyloxy)-3-methylphenyl]-N-′-(2-nitrobenzoyl) -N-(2-nitrophenylathio)urea (Compound No. 38)

(1) 2.0 g of 4-(5 chloro-2-pyrimidinyloxy)-3methylaniline and 0.94 g of triethylamine were dissolved in 20 ml of toluene, and a solution of 1.61 g of 2-nitrobenzenesulfenyl chloride dissolved in 5 ml of toluene was dropwise added thereto at room temperature. The mixture was reacted at room temperature for 1 hour under stirring. After completion of the reaction, ethyl acetate was added to the reaction product, and the ethyl acetate layer was washed with water, dried over Glauber's salt and then purified by column chromatography to obtain 2.76 g of N-[4-(5-chloro-2-pyrimidinyloxy)-3-methylphenyl]-2-nitrobenzenesulfenamide (Intermediate Compound No. 37) (melting point: 74°–85° C.) in a yellow non-crystalline form.

(2) 2.0 g of the Intermediate Compound No. 37 obtained in the above step (1) was dissolved in 30 ml of toluene, and 1.48 g of 2-nitrobenzoyl isocyanate was added thereto. The mixture was reacted at room temperature for 2 hours. After completion of the reaction, 20 ml of n-hexane was added to the reaction product, and the mixture was subjected to filtration. The crystals thereby obtained were washed with methanol to obtain 2.85 g of the desired compound (melting point: 171°–174° C.) as slightly yellow crystals.

PREPARATION EXAMPLE 4

Preparation of N-[4-(5-chloro-2-pyrimidinyloxy)-3-methylphenyl]-N′-(2-nitrobenzoyl)-N-valerylurea (Compound No. 12)

(1) 2.0 g of 4-(5-chloro-2-pyrimidinyloxy)-3-methylaniline and 1.3 ml of triethylamine were dissolved in 20 ml of tetrahydrofuran, and 1.12 ml of valeryl chloride was dropwise added thereto under cooling with ice. The mixture was reacted at room temperature for 40 minutes under stirring. After completion of the reaction, the reaction product was poured into water and extracted with ethyl acetate. The extract layer was washed with a saturated aqueous solution of sodium chloride and dried over Glauber's salt. Then, ethyl acetate was distilled off to obtain 2.8 g of N-[4-(5-chloro-2-pyrimidinyloxy)-3-methylphenyl]valeramide (Intermediate Compound No. 13) (melting point: 146°–150° C.)

(2) 2.0 g of the Intermediate Compound No. 13 obtained in the above step (1) and 2.43 g of 2-nitrobenzoyl isocyanate were dissolved in 40 ml of tetrahydrofuran, and the mixture was reacted under reflux for 2.5 hours. After completion of the reaction, tetrahydrofuran was distilled off under reduced pressure from the reaction product, and the reaction product was purified by silica gel column chromatography to obtain 1.65 g of the desired compound (melting point: 69°–75° C.) in a non-crystalline form.

PREPARATION EXAMPLE 5

Preparation of N-[4-(5-bromo-2-pyrimidinyloxy)-3-methylphenyl]carbamoyl-1-methylbutyl 2-nitrobenzimidate (Compound no. 71)

(1) 9 g of fluorosulfonic acid was cooled to −78° C. with dry ice-acetone, 30 ml of 1-pentene was gradually dropwise added thereto under stirring. After completion of the dropwise addition, the stirring was continued at the same temperature for 15 minutes. 100 ml of methylene chloride which was previously cooled to −78° C., was added thereto, and then 15 g of 2-nitrobenzamide was added thereto at once. Then, the reaction was conducted for 12 hours under stirring while the temperature of the solution was returned to room temperature. After completion of the reaction, the reaction solution was poured into a mixture of 250 ml of a 1N sodium hydroxide aqueous solution and 100 ml of methylene chloride, which was cooled to 0° C., and then the mixture was vigorously stirred for 10 minutes. The reaction solution was extracted, and the extract was washed with water and then dried over Glauber's salt. After distillation of the solvent, the residue was purified by silica gel column chromatography to obtain 0.3 g of oily 1-methylbutyl 2-nitrobenzimidate (Intermediate Compound No. 63).

(2) 0.5 g of 4-(5-bromo-2-pyrimidinyloxy)-3-methylphenyl isocyanate obtained by reacting 0.4 g of 4-(5-bromo-2-pyrimidinyloxy)-3-methylaniline with 0.4 ml of trichloromethyl chloroformate, was dissolved in 10 ml of toluene, and 0.3 g of the Intermediate Compound No. 63 obtained in the above step (1) was dropwise added to the solution. Then, the mixture was reacted at the same temperature for 1.5 hours under stirring. After completion of the reaction, toluene was distilled off under reduced pressure from the reaction product, and the residue was purified by silica gel column chromatography to obtain 0.35 g of the desired compound (melting point: 54°–58° C.).

Now, typical examples of the compound of the formula I will be described in Tables 3 and 4.

TABLE 3

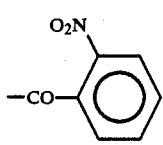

| Compound No. | X | R³ | R¹ | (Y)_m | (R⁸)_r | Physical properties Melting point (°C.) |
|---|---|---|---|---|---|---|
| 1 | H | $NO_2$ | $-COC_2H_5$ | 3-$CH_3$ | 5-Cl | 96–101 |
| 2 | " | " | $-COC_7H_{15}(n)$ | " | 5-Br | 57–61 |
| 3 | " | " | $-COC_4H_9(n)$ | " | " | 65–82 (Non-crystalline form) |
| 4 | " | " | $-COC_{11}H_{23}(n)$ | " | " | 40–44 (Non-crystalline form) |
| 5 | " | " | $-COC_{10}H_{21}(n)$ | " | " | 42–47 (Non-crystalline form) |
| 6 | " | " | $-COC_5H_{11}(n)$ | " | " | 64–68 (Non-crystalline form) |
| 7 | " | " | $-COC_5H_{11}(n)$ | " | 5-Cl | 61–64 (Non-crystalline form) |
| 8 | " | " | $-COC_6H_{13}(n)$ | " | 5-Br | 49–58 (Non-crystalline form) |
| 9 | " | " | $-COC_3H_7(n)$ | " | 5-Cl | 60–67 (Non-crystalline form) |
| 10 | " | " | $-COC_3H_7(n)$ | " | 5-Br | 71–77 (Non-crystalline form) |
| 11 | " | " | $-COC_6H_{13}(n)$ | " | 5-Cl | 56–62 (Non-crystalline form) |
| 12 | H | $NO_2$ | $-COC_4H_9(n)$ | 3-$CH_3$ | 5-Cl | 69–75 (Non-crystalline form) |
| 13 | " | " | $-COCH_3$ | 3-Cl | 5-Br | 130–135 |
| 14 | " | " | " | 3-$CH_3$ | " | 99–103 |
| 15 | " | " | $-COCH=CH_2$ | " | " | 66–75 (Non-crystalline form) |
| 16 | " | " | $-COC\equiv CH$ | " | " | |
| 17 | " | " | 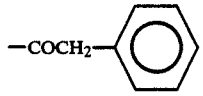 | 2,3-$F_2$ | " | |
| 18 | 4-Cl | " | $-COC_4H_9(n)$ | 3-$CH_3$ | 4,6-$(CH_3)_2$ | |
| 19 | H | " | $-COCH_2CF_3$ | " | 5-Br | |
| 20 | " | " | 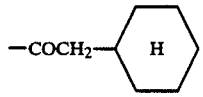 | " | " | |
| 21 | " | " | 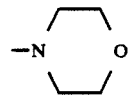 | " | " | |
| 22 | " | –N(morpholino)O | $-COC_2H_5$ | " | " | |

TABLE 3-continued

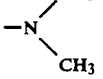

| Compound No. | X | R³ | R¹ | (Y)ₘ | (R⁸)ᵣ | Physical properties Melting point (°C.) |
|---|---|---|---|---|---|---|
| 23 | 6-F | —N(CH₃)CH₃ | " | " | " | |
| 24 | H | NO₂ | —S—N(CH₃)—CO₂CH(CH₃)₂ | " | 5-Cl | 80–86 (Non-crystalline form) |
| 25 | H | NO₂ | —S—N(C₂H₅)—SO₂CH₃ | 3-CH₃ | 5-Cl | 107–115 (Non-crystalline form) |
| 26 | " | " | —S—N(CH₃)—CO₂CH₃ | " | " | 83–88 |
| 27 | " | " | —S—N(C₃H₇(n))—CO₂CH(CH₃)₂ | " | " | 67–70 |
| 28 | " | " | —S—N(CH₃)—CO₂CH(CH₃)₂ | 3-Cl | 5-Br | 79–105 (Non-crystalline form) |
| 29 | " | " | —S—N(C₃H₇(n))—CO₂CH(CH₃)₂ | " | " | 71–77 (Non-crystalline form) |
| 30 | " | " | —S—N(CH₃)—CO₂—C₆H₅ | " | " | 89–96 (Non-crystalline form) |
| 31 | " | " | —S—N(C₈H₁₇(n))—CO₂CH₃ | " | " | 51–54 (Non-crystalline form) |
| 32 | " | " | —S—N(CH₃)—CO₂C₈H₁₇(n) | " | " | 57–63 (Non-crystalline form) |
| 33 | " | " | —S—N(CH₃)—CO₂CH(CH₃)₂ | 3-CF₃ | 5-Cl | 86–92 |
| 34 | H | NO₂ | —S—N(CH₃)—CO₂CH(CH₃)₂ | 3-NO₂ | 5-Br | 72–98 (Non-crystalline form) |
| 35 | 4-Cl | " | —S—N(CH₃)—CO₂CH(CH₃)₂ | 3-CH₃ | 5-Cl | 88–92 |
| 36 | H | " | —S—CO₂CH₃ | " | " | 92–99 (Non-crystalline form) |
| 37 | " | " | —S—C₁₀H₂₁(n) | " | 5-Br | About 35 (Viscous semi-solid) |

TABLE 3-continued

Structure:
5,6-position phenyl ring with X at 4, R³ at 2 — C1 — CONHCON(R¹) — phenyl ring (positions 2,3,5,6 with (Y)ₘ) — O — pyrimidine ring (positions 4,5,6 with (R⁸)ᵣ, N at positions where shown)

| Compound No. | X | R³ | R¹ | (Y)ₘ | (R⁸)ᵣ | Physical properties Melting point (°C.) |
|---|---|---|---|---|---|---|
| 38 | " | " | —S—(2-NO₂-phenyl) | " | 5-Cl | 171–174 (Slightly yellow) |
| 39 | " | " | —S—phenyl | " | " | 74–77 (Non-crystalline form) |
| 40 | " | " | —S—phenyl | " | 5-Br | 80–88 (Non-crystalline form) |
| 41 | " | " | —S—CO₂CH₃ | 3-Cl | " | 103–107 |
| 42 | " | " | —S—(2-NO₂-phenyl) | " | " | 183–185 (Slightly yellow) |
| 43 | " | " | —S—C₄H₉(n) | " | " | 63–67 (Non-crystalline form) |
| 44 | " | " | —S—C₁₀H₂₁(n) | " | " | Oily substance |
| 45 | " | " | —O—C₄H₉(n) | 3-CH₃ | " | |
| 46 | 4-Cl | NO₂ | —SCH=CH₂ | 3-CH₃ | 4,6-(CH₃)₂ | |
| 47 | H | " | —SC≡CH | 2,3-F₂ | 5-Br | |
| 48 | " | " | —SCH₂CF₃ | 3-CH₃ | " | |
| 49 | " | " | —S—CH₂—cyclohexyl(H) | " | " | |
| 50 | " | " | —SN(CH₃)₂ | " | " | |
| 51 | " | " | —S—(2-CN-phenyl) | " | " | |
| 52 | " | " | —P(=S)(OC₂H₅)₂ | " | " | 56–60 (Non-crystalline form) |
| 53 | " | " | —P(=O)(OC₂H₅)(SC₂H₅) | " | " | |

TABLE 3-continued

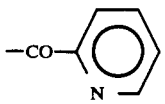

| Compound No. | X | R³ | R¹ | (Y)ₘ | (R⁸)ᵣ | Physical properties Melting point (°C.) |
|---|---|---|---|---|---|---|
| 54 | " | " | —CO—(pyridyl) | " | " | |

Compound No. 55:
Isopropyl 4-[3-(5-chloro-2-pyrimidinyloxy)-4-methylphenyl]-7-(2-nitrophenyl)-2-methyl-5,7-dioxo-3-thia-2,4,6-triazaheptanate
Melting point: 72°–84° C. (Non-crystalline form)

Compound No. 56:
Isopropyl 4-[4-(6-chloro-3-pyridazinyloxy)-3chloropheny]-7-(2-nitrophenyl)-2-methyl-5,7-dioxo-3-thia-2,4,6-triazaheptanate
Melting point: 96°–105° C. (Non-crystalline form)

Compound No. 57:
Isopropyl 4-[4-(5-nitro-2-pyridinyloxy)-3-chlorophenyl]-7-(2-nitrophenyl)-2-methyl-5,7-dioxo-3-thia-2,4,6-triazaheptanate
Melting point: 85°–91° C. (Non-crystalline form)

Compound No. 58:
N-[3-methyl-4-(4,5,6-trimethyl-2-pyridinyloxy]-phenyl]-N'-(2-nitrobenzoyl)-N-propionylurea

TABLE 4

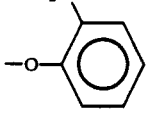

| Compound No. | X | R³ | R² | (Y)ₘ | (R⁸)ᵣ | Physical properties Melting point (°C.) |
|---|---|---|---|---|---|---|
| 59 | H | NO₂ | —OCH₃ | 3-Cl | 5-Br | 153–155 |
| 60 | " | " | —OC₂H₅ | " | " | 183–184 |
| 61 | " | " | —OC₃H₇(iso) | " | " | 81–85 |
| 62 | " | " | —OC₅H₁₁(sec) | " | " | 63–65 |
| 63 | " | " | —OC₁₀H₂₁(n) | " | " | 92–93 |
| 64 | " | " | —OCH₃ | 3-CF₃ | " | 83–85 |
| 65 | " | " | —OCH₃ | " | 5-Cl | 68–69 |
| 66 | " | " | —OC₂H₅ | " | 5-Br | 82–84 |
| 67 | " | " | —OC₃H₇(iso) | " | " | 70–73 |
| 68 | " | " | —OCH₃ | 3-CH₃ | " | 79–81 |
| 69 | " | " | —OC₂H₅ | " | " | 103–104 |
| 70 | " | " | —OC₃H₇(iso) | " | " | 71–74 |
| 71 | " | " | —OC₅H₁₁(sec) | " | " | 54–58 |
| 72 | " | " | —OC₅H₁₁(n) | " | " | (Non-crystalline form) |
| 73 | " | " | —OC₁₀H₂₁(n) | " | " | 75–76 |
| 74 | 4-Cl | " | —OCH₂CH=CH₂ | 2,3-F₂ | " | |
| 75 | H | " | —OCH₂C≡CH | 3-CH₃ | 4,6-(CH₃)₂ | |
| 76 | " | " | —O—(O₂N-phenyl) | " | 5-Br | |
| 77 | " | " | —O—(Cl-pyridyl) | " | " | |
| 78 | 6-F | —N(CH₃)₂ | —OC₂H₅ | 3-CH₃ | 5-Br | 60–63° C. |

TABLE 4-continued

Structure: phenyl ring (positions 2,3,4,5,6) with X at 4, $R^3$ at 3, $R^2$ on C=NCONH— connecting to another phenyl ring (positions 2,3,4,5,6) with $(Y)_m$ and O at 4, linked to pyrimidine-like ring (N at 1,3 positions) bearing $(R^8)_r$.

| Compound No. | X | $R^3$ | $R^2$ | $(Y)_m$ | $(R^8)_r$ | Physical properties Melting point (°C.) |
|---|---|---|---|---|---|---|
| 79 | H | —N(pyrrolidinyl) | " | " | " | |
| 80 | " | $NO_2$ | —OCH$_2$—(cyclohexyl) | " | " | |
| 81 | " | " | —OCH$_2$—(phenyl) | " | " | |
| 82 | " | " | —OCH$_2$CF$_3$ | " | " | |
| 83 | " | " | —SCH$_2$—(cyclohexyl) | " | " | (Non-crystalline form) |
| 84 | " | " | —SCH$_2$CH=CH$_2$ | " | " | (Non-crystalline form) |
| 85 | " | " | —SCH$_2$C≡CH | " | " | (Non-crystalline form) |
| 86 | " | " | —OC$_2$H$_5$ | " | 5-Cl | 145–146 |
| 87 | " | " | " | 3-OCH$_3$ | " | 152–153 |
| 88 | " | " | —OCH$_2$—(cyclopentyl) | 3-CH$_3$ | 5-Br | 59–60 |
| 89 | " | " | —SC$_2$H$_5$ | " | " | 80–88 |
| 90 | " | " | —SC$_5$H$_{11}$(sec) | " | " | (Non-crystalline form) |
| 91 | " | " | —OC$_2$H$_5$ | 2,3-F$_2$ | 5-Cl | Non-crystalline form |
| 92 | " | " | " | 2,3,5,6-F$_4$ | 5-Br | 140–148 |

Compound No. 93:
N-[3-(5-bromo-2-pyrimidinyloxy)-4-methylphenyl]-carbamoyl-1-methylbutyl 2-nitrobenzimidate Compound No. 94:
N-[4-(6-bromo-3-pyridazinyloxy)-3-methylphenyl]-carbamoyl-1-methylbutyl 2-nitrobenzimidate Compound No. 95:
N-[4-(5-bromo-2-pyridinyloxy)-3-methylphenyl]carbamoyl-1-methylbutyl 2-nitrobenzimidate The compound of the formula I is effective against cancers in experimental animals e.g. mice such as P-388 leukemia, L -1210 leukemia, B-16 melanoma, N-5076 sarcoma, Colon 38, Colon 26 and Leuis lung carcinoma. On the other hand, certain in vivo test systems and protocols have been developed by National Cancer Institute for testing compounds to determine their suitabilities as antineoplastic agents. These have been reported in "Cancer Chemotherapy Reports", Part III, Vol. 3, No. 2 (1972) written by Deran, Greenberg, MacDonald, Schumacher and Abott. These protocols have established standardized screening tests which are generally followed in the field of testing for antitumour agents. Among these systems, P-388 leukemia is particularly significant for the present invention. These neoplasms were discovered in mice. Excellent antitumour activities indicated by the percent increase of the average life span of treated animals (T) over control animals (C) in these protocols generally suggest the same results against human leukemia.

Now, the antitumour activities, doses and methods of administration of the compounds of the formula I will be described. These compounds exhibit excellent antitumour activities.

(1) Antitumour activities

TEST EXAMPLE 1 (Intraperitoneally transplanted-intraperitoneally administered) $1 \times 10^6$ of P-388 leukemia cell per mouse were intraperitoneally transplanted to BDF$_1$ mouse. Each formulation was intraperitoneally administered 1 and 8 days after the transplantation.

The mortality was observed for 30 days. The increase life span of each group was determined on such basis that the survival time of a control group to which physiological saline was administered was regarded to be 0% of increase life span (ILS). The results are shown in Table 5. Each formulation was formed in accordance with the below-mentioned Formulation Example 8.

TABLE 5

| Compound No. | Dose (active ingredient mg/kg/day) | Increase life span* (ILS) (%) |
|---|---|---|
| 1 | 50 | 136 |
|  | 25 | 62 |
| 24 | 12.5 | 65 |
|  | 6.25 | 24 |
| 25 | 6.25 | 58 |
| 28 | 25 | 92 |
|  | 12.5 | 43 |
| 29 | 12.5 | 143 |
| 33 | 6.25 | 71 |
| 36 | 12.5 | 90 |
|  | 6.25 | 28 |
| 41 | 12.5 | 74 |
| 55 | 3.125 | 35 |
| 57 | 200 | >108 |
|  | 100 | 71 |
| 60 | 25 | 105 |
|  | 12.5 | 21 |
| 61 | 100 | 153 |
|  | 50 | 47 |
| 63 | 100 | 43 |
| 64 | 12.5 | 45 |
| 65 | 25 | 163 |
|  | 12.5 | 61 |
| 66 | 6.25 | 89 |
|  | 3.125 | 21 |
| 67 | 6.25 | 59 |
| 68 | 100 | 147 |
|  | 50 | 35 |
| 69 | 6.25 | 105 |
| 70 | 6.25 | 59 |
| 71 | 50 | 194 |
|  | 25 | 59 |
| 72 | 12.5 | 99 |
| 73 | 25 | 54 |

(Note)
*Increase life span is calculated by the following equation:

$$\text{Increase life span \% (ILS)} = \left( \frac{\text{Survival time of test group}}{\text{Survival time of control animals}} \times 100 \right) - 100$$

TEST EXAMPLE 2 (interperitoneally transplanted - orally administered)

$1 \times 10^6$ of P-388 leukemia cells per mouse were intraperitoneally transplanted to BDF$_1$ mouse. Each formulation was orally administered 1 and 8 days after the transplantation. The mortality was observed for 30 days. The increase life span of each group was determined in the same manner as in Test Example 1 on such basis that the survival time of a control group to which a physiolosical saline was administered was regarded to be 0% of increase life span (ILS). The results are shown in Table 6. The formulations of Compound Nos. 4 to 12, 23, 29, 31, 32, 35 and 37 were formed in accordance with the below-mentioned Formulation Example 9, and the formulations of other compounds were formed in accordance with Formulation Example 8.

TABLE 6

| Compound No. | Dose (Active ingredient mg/kg/day) | Increase life span (ILS) (%) |
|---|---|---|
| 1 | 25 | 80 |
| 2 | 25 | 89 |
|  | 12.5 | 21 |
| 3 | 25 | 138 |
|  | 12.5 | 99 |
| 4 | 100 | 161 |
|  | 50 | 36 |
| 5 | 100 | 136 |
|  | 50 | 55 |
| 6 | 25 | 90 |
| 7 | 50 | 193 |
|  | 25 | 55 |
| 8 | 25 | 124 |
|  | 12.5 | 21 |
| 9 | 50 | 156 |
| 10 | 50 | 187 |
|  | 25 | 32 |
| 11 | 25 | 64 |
| 12 | 50 | 133 |
|  | 25 | 55 |
| 13 | 50 | 60 |
|  | 25 | 21 |
| 15 | 25 | 76 |
| 24 | 12.5 | 105 |
|  | 6.25 | 42 |
| 25 | 12.5 | 53 |
|  | 6.25 | 42 |
| 26 | 25 | >128 |
| 27 | 12.5 | 160 |
|  | 6.25 | 41 |
| 28 | 200 | 171 |
| 29 | 3.125 | 93 |
| 30 | 12.5 | 31 |
| 31 | 50 | 42 |
| 32 | 50 | 121 |
|  | 25 | 50 |
| 33 | 6.25 | 182 |
|  | 3.125 | 37 |
| 34 | 200 | 134 |
|  | 100 | 25 |
| 35 | 12.5 | 53 |
| 36 | 6.25 | 31 |
| 37 | 6.25 | 32 |
| 38 | 50 | 122 |
|  | 25 | 99 |
| 39 | 25 | 147 |
| 40 | 12.5 | 124 |
|  | 6.25 | 32 |
| 41 | 25 | 89 |
|  | 12.5 | 39 |
| 42 | 12.5 | 84 |
|  | 6.25 | 63 |
| 43 | 50 | 148 |
|  | 25 | 45 |
| 44 | 100 | 158 |
|  | 50 | 34 |
| 52 | 50 | 90 |
|  | 25 | 21 |
| 55 | 100 | 80 |
|  | 50 | 69 |
| 56 | 200 | 71 |
|  | 100 | 34 |
| 57 | 800 | 192 |
|  | 400 | 134 |
| 59 | 200 | 86 |
| 60 | 200 | 50 |
|  | 100 | 38 |
| 61 | 400 | 165 |
|  | 200 | 73 |
| 62 | 200 | 143 |
|  | 100 | 95 |
| 63 | 400 | 54 |
| 64 | 50 | 196 |
|  | 25 | 97 |
| 65 | 50 | 174 |
|  | 25 | 32 |

TABLE 6-continued

| Compound No. | Dose (Active ingredient mg/kg/day) | Increase life span (ILS) (%) |
|---|---|---|
| 66 | 12.5 | 242 |
|  | 6.25 | 175 |
| 67 | 25 | 156 |
|  | 12.5 | 36 |
| 68 | 100 | 100 |
|  | 50 | 85 |
| 69 | 25 | 135 |
|  | 12.5 | 54 |
| 70 | 50 | 118 |
|  | 25 | 35 |
| 71 | 200 | 212 |
|  | 100 | 147 |
| 72 | 12.5 | 105 |
|  | 6.25 | 29 |
| 73 | 100 | 99 |
|  | 50 | 69 |
| 83 | 50 | 60 |
|  | 25 | 21 |
| 84 | 50 | 60 |
|  | 25 | 50 |
| 85 | 50 | 60 |
|  | 25 | 31 |
| 86 | 25 | 98 |
|  | 12.5 | 32 |
| 87 | 400 | 53 |
|  | 200 | 23 |

TEST EXAMPLE 3 (Intraperitoneally transplanted - orally administered)

A suspension of B-16 melanoma cells was intraperitoneally inoculated to $BDF_1$ mice in an amount of 0.5 ml/mouse. Each formulation was orally administered 1, 8 and 15 days after the inoculation. The mortality of the mice were observed for 60 days. The percent increase life span (ILS) of each group was determined on such basis that the survival time of a control group to which a physiological saline was administered was regarded to be 0% of increase life span (ILS). The results are shown in Table 7. Each formulation was formed in accordance with the below-mentioned Formulation Example 4. The suspension of B-16 melanoma cells was obtained by taking out the melanoma under aseptic condition, which was successively subcutaneously tranplanted in C57BL/6 mouse, and then passing the melanoma through a stainless steel mesh and dispersing 1 g of the melanoma cells in 9 ml of an isotonic solution such as a culture medium or a physiological saline.

TABLE 7

| Compound No. | Dose (Active ingredient mg/kg/day) | Increase life span (ILS) (%) |
|---|---|---|
| 24 | 25 | 61 |
| 34 | 400 | 36 |
| 71 | 50 | 75 |
|  | 25 | 47 |
| 72 | 25 | 42 |
|  | 12.5 | 32 |
| 73 | 25 | 31 |

The compound of the formula I exhibits high antitumour activities in either case where the inoculated site of cancer cells and the administered site of the formulation are the same or different. The reason is not clear. However, this may be attributable to the fact that the compound of the present invention is excellent in the absorbability in digestive tract, in the concentration in blood and in the transferability to a target site.

(2) Dose and method for administration

As the method for administration, in the case of animals, drugs may be administered by injection such as intraperitonial injection, intraveneous injection or local administration, or by oral administration. In the case of human beings, drugs may be administered by injection such as intravascular injection to a vein or an artery or local administration, by oral administration, or as a suppository. The dose is determined in view of the results of animal experiments and various conditions within a range that the total amount does not exceed a certain amount. Drugs may be administered continuously or intermittently. However, the dose may optionally vary depending upon the method for administration, the patient or the condition of an animal to be treated such as age, body weight, sex, sensitivity, food, time of administration, drugs used together or degree of the patient or the disease. The suitable amount and the numbers of administration under a certain condition, must be determined by the determination test of a suitable amount by a specialist based on the above guide line.

The antitumour agent of the present invention may be formulated in the same manner as in the case of usual drugs. It is formulated from the active ingredient and various pharmaceutically acceptable adjuvants such as an inert diluent. The formulation is most preferably administered orally or intervaneously, or in the form of a suppository.

Further, the content of the active ingredient in the antitumour agent of the present invention varies depending upon the difference of various conditions and can not generally be defined. The agent may contain the active ingredient in the same manner as in the case of usual antitumour agents. For example, it may contain at least 0.001% of the active ingredient.

The compound of the formula I is readily soluble in an organic solvent as compared with conventional compounds, and various formulations or methods for administration are applicable. For example, as regards formulations, there may be mentioned a suppository or a capsule formulated by directly mixing the compound with polyethylene glycol, or an aqueous suspension. When the compound of the formula I is formulated into an aqueous suspension, it may contain a phospholipid. As the method for formulating an aqueous suspension which does not contain a phospholipid, there may be mentioned for example, a method wherein the active ingredient compound previously formed into fine powder, is added to an aqueous solution containing a surfactant and if necessary, a defoaming agent, the mixture is then subjected to wet pulverization to obtain particles having a particle size of at most 5 $\mu$m, for example, particles of which 80% have a particle size of at most 2 $\mu$m, and, if necessary, a thickener is added thereto. The surfactant includes, for example, polyoxyethylene hardened castor oil, polyoxyethylene sorbitol fatty acid ester, sucrose ester, polyoxyethylene-polyoxypropylene block polymer and oxyethylated polyarylphenol phosphate. The defoaming agent includes, for example, dimethylpolysiloxane, methylphenylsiloxane, sorbitolaliphatic acid ester, polyoxyethylene polyoxypropylenecetyl ether and silicone. The thickener includes, for example, Guar gum, arginic acid, gum arabic, pectin, starch, xanthane gum and gelatin. On the other hand, as the method for formulating an aqueous suspension containing a phospholipid, there may be mentioned, for example, a method wherein a phospholipid such as soy bean phospholipid or yolk phospholipid is used instead of the surfactant used in the above method, and an antioxidant such as α-tocopherol is used instead of the thickener.

Further, these formulations may be formed into tablets, capsules, enteric-coated tablets, powders, injection solutions or suppositorties by usual methods commonly employed in the field of formulation. Now, specific Formulation Examples of the antitumour agent of the present invention will be mentioned.

FORMULATION EXAMPLE 1

70 mg of non-crystalline powder of the compound of the formula I was thoroughly mixed with 30 mg of lactose, and mixture was filled in capsules in an amount of 100 mg per capsule to obtain capsules for oral administration.

FORMULATION EXAMPLE 2

85 parts by weight of the non-crystalline powder of the compound of the formula I was uniformly mixed with 1 part by weight of glucose, 10 parts by weight of corn starch and 1.5 parts by weight of a 5% corn starch paste solution. The mixture was formed to granules by a wet method. Then, 1 part by weight of magnesium stearate was added thereto, and the mixture was tabletted by compression to obtain tablets for oral administration.

FORMULATION EXAMPLE 3

5 g of the compound of the formula I was dissolved in 5 ml of dimethyl acetamide, and 25 ml of coconut oil, 7 g of Pegnol HC-17 (registered trademark, hardened caster oil manufactured by Toho Kagaku) and 6 g of Pegnol HO-10M (registered trademark, sucrose ester manufactured by Toho Kagaku) were added thereto to obtain an emulsion. To this emulsion, the same amount of sterilized distilled water was added, and the mixture was subjected to ultrasonic treatment for 20 to 30 seconds to obtain an oily suspension.

FORMULATION EXAMPLE 4

The compound of the formula I was preliminarily pulverized to fine powder by a centrifugal pulverizer. On the other hand, 5 parts by weight of polyoxyethylene (60) hardened castor oil 0.2 part by weight of silicone and 0.3 part by weight of polyoxyethylenepolyoxypropylene block polymer were added to 79.5 parts by weight of a physiological saline to obtain an aqueous solution. To the aqueous solution, 10 parts by weight of the fine powder of the compound of the formula I was added. The mixture was wet pulverized by a sand mill by using glass beads (particles of which 80% had a particle size of at most 2 682 m). Then, 5 parts by weight of a 2% xanthane gum solution was added thereto to obtain an aqueous suspension.

FORMULATION EXAMPLE 5

40 parts by weight of the compound of the formula I was added to an aqueous solution containing 1.5 parts by weight of oxyethylated polyarylphenol phosphate and 0.2 part by weight of silicone dissolved in 53.3 parts by weight of a physiological saline. The mixture was wet pulverized by a sand mill by using glass beads (particles of which 90% had a particle size of at most 2 μm). Then, 5 parts by weight of a 2% xanthane gum solution was added thereto to obtain an aqueous suspension.

FORMULATION EXAMPLE 6

The compound of the formula I was preliminarily pulverized to fine powder by a centrifugal pulverizer. 5 parts by weight of the fine powder of the compound of the formula I was added to an aqueous solution obtained by dispersing and stirring 2 parts by weight of yolk phospholipid, 0.001 part by weight of α-tocopherol and 92.999 parts by weight of a physiological saline. The mixture was wet pulverized by a sand mill by using glass beads (particles of which 80% had a particle size of at most 2 μm) to obtain an aqueous suspension.

FORMULATION EXAMPLE 7

The compound of the formula I was preliminarily pulverized to fine powder by a centrifugal pulverizer. On the other hand, 5 parts by weight of polyoxyethylene (60) hardened castor oil was added to 60 parts by weight of a physiological saline to obtain an aqueous solution. To the aqueous solution, 30 parts by weight of the fine powder of the compound of the formula I was added. The mixture was wet pulverized by a sand mill by using glass beads (particles of which 80% had a particle size of at most of 2 μm). Then, 5 parts by weight of a 2% xanthane gum solution was added thereto to obtain an aqueous suspension.

FORMULATION EXAMPLE 8

10 parts by weight of the compound of the formula I was added to an aqueous solution containing 1.5 parts by weight of oxyethylated polyaryl phosphate, 0.2 part by weight of silicon and 0.3 part by weight of polyoxyethylene-polyoxypropylene block polymer dissolved in 80 parts by weight of a physiological saline. The mixture was wet pulverized by a sand mill by using glass beads (particles of which 90% had a particle size of at most 2 μm). Then, 7 parts by weight of a 2% xanthane gum solution was added thereto to obtain an aqueous suspension.

FORMULATION EXAMPLE 9

To 1 part by weight of the compound of the formula I, 100 parts by weight of polyethyleneglycol # 400 (molecular weight: 380–420, manufactured by Nakarai Kagaku Yakuhin) was added and dissolved to obtain a homogeneous solution.

We claim:

1. A compound of the formula

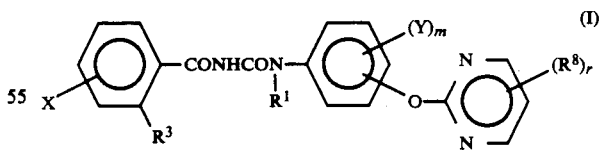

or

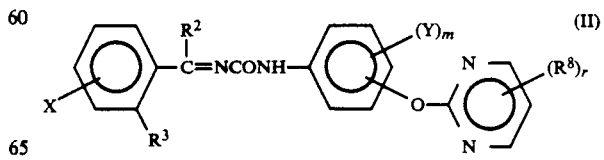

or a salt thereof
wherein:

X is selected from the group consisting of hydrogen, halogen and nitro;

$R_1$ is selected from the group consisting of

—$X^1Z^1$,

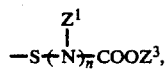

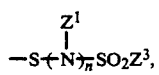

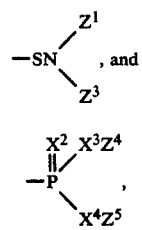

wherein each of $Z^1$, $Z^3$, $Z^4$ and $Z^5$ is independently selected from the group consisting of alkyl of 1 to 11 carbon atoms, substituted alkyl of 1 to 11 carbon atoms, alkenyl of 2 to 6 carbon atoms, substituted alkenyl of 2 to 6 carbon atoms, alkynyl of 2 to 6 carbon atoms, substituted alkynyl of 2 to 6 carbon atoms, phenyl, substituted phenyl, naphthyl, substituted naphthyl, thienyl, substituted thienyl, furyl, substituted furyl, pyranyl, substituted pyranyl, pyridinyl, substituted pyridinyl, pyrimidinyl, substituted pyrimidinyl, quinolyl, substituted quinolyl, quinoxalinyl, and substituted quinoxalinyl; and each of $X^1$, $X^2$, $X^3$ and $X^4$ is independently selected from the group consisting of oxygen and sulfur;

$R^2$ is selected from the group consisting of —$OZ^1$ and —$SZ^1$, wherein $Z^1$ is as defined above;

$R^3$ is selected from the group consisting of nitro, dialkylamino wherein each alkyl has from 1 to 6 carbon atoms, morpholino, aziridinyl, pyrrolidinyl and piperidino;

Y is selected from the group consisting of halo, alkyl of 1 to 11 carbon atoms, substituted alkyl of 1 to 11 carbon atoms, alkoxy of 1 to 11 carbon atoms, substituted alkoxy of 1 to 11 carbon atoms, alkylthio of 1 to 11 carbon atoms, substituted alkylthio of 1 to 11 carbon atoms, nitro or

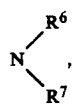

wherein $R^6$ and $R^7$ are independently from the group consisting of alkyl of 1 to 11 carbon atoms and substituted alkyl of 1 to 11 carbon atoms;

m is an integer from 1 to 4, inclusive;

n is zero or 1; and $(R^8)_4$ is selected from 1 to 3 halo, nitro or $C_1$-$C_{11}$- alkyl substituents or a single substituent defined above for Y other than halo, nitro or alkyl, located at the 5-position of the pyrimidine ring;

and the substituents of the substituted alkyl, alkenyl, alkynyl, phenyl, naphthyl, thienyl, furyl, pyranyl, pyridinyl, pyrimidinyl, quinolyl and quinoxalinyl, groups in the definitions of $Z^1$, $Z^3$, $Z^4$ and $Z^5$ are selected from the group consisting of halo, nitro, cyano, alkyl of 1 to 11 carbon atoms, haloalkyl of 1 to 11 carbon atoms, alkenyl of 2 to 6 carbon atoms, haloalkenyl of 2 to 6 carbon atoms, alkynyl of 2 to 6 carbon atoms, haloalkynyl of 2 to 6 carbon atoms, cycloalkyl of 3 to 6 carbon atoms, halocycloalkyl of 3 to 6 carbon atoms, phenyl and halophenyl, and the substituent of the substituted alkyl, the substituted alkoxy and the substituted alkylthio groups in the definitions of Y, $R^6$, $R^7$ and $R^8$ is a halogen atom.

2. A compound of claim 1 of the formula (I).

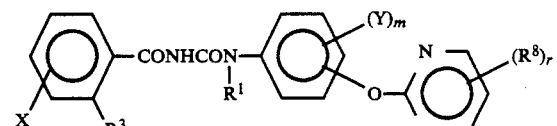

3. A compound or its salt according to claim 2, wherein X is a hydrogen atom, $R^3$ is a nitro group and $R^1$ is —$SZ^1$ or —$COZ^1$.

4. A compound of claim 1 of the formula (II).

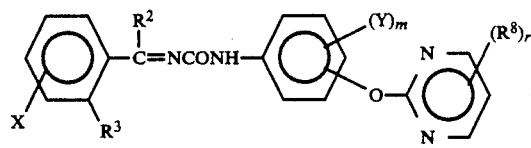

5. A compound or its salt according to claim 4, wherein X is a hydrogen atom, $R^3$ is a nitro group and $R^2$ is —$OZ^1$.

6. A compound or its salt according to claim 1, wherein Y is alkyl or haloalkyl of 1 to 11 carbons and m is 1.

7. A compound or its salt according to claim 6, wherein Y is methyl or halomethyl.

8. A compound of claim 1 wherein $R^8$ is located at the 5-position and r is 1.

9. A compound of claim 8, wherein $R^8$ is 5-halo.

10. A compound or its salt according to claim 1, wherein the compound is N-N'-(2-nitrobenzoyl)-N-valerylurea, N-N'-(2-nitrobenzoyl)-N'-undecanoylurea, N-N-hexanoyl-N'-(2-nitrobenzoyl)urea, N-N-hexanoyl-N'-(2-nitrobenzoyl)urea, N-N-heptanoyl-N'-(2-nitrobenzoyl)urea, N-butyryl-N-N'-(2-nitrobenzoyl)urea, N-N-butyryl-N'-(2-nitrobenzoyl)urea, N-N'-(2-nitrobenzoyl)-N-valerylurea, N-N'-(2-nitrobenzoyl)-N-(2-nitrophenylthio)urea, N-N-butylthio-N'-(2-nitrobenzoyl)urea, N-carbamoyl 1-methylbutyl-2-nitrobenzimidate, or N-carbamoylpentyl 2-nitrobenzimidate.

11. A composition for treating leukemia or melanoma in a mammal, comprising:
 a compound or its salt as defined in claim 1 in an amount sufficient to exhibit a controlling activity against leukemia or melanoma in combination with a pharmaceutically acceptable adjuvant.

12. A method of treating leukemia or melanoma in a mammal, which comprises:
 administering a compound or its salt as defined in claim 1 in an amount sufficient to exhibit a controlling activity against said leukemia or melanoma.

* * * * *